United States Patent [19]

Fattaleh

[11] 4,123,845
[45] Nov. 7, 1978

[54] SELF CONTAINED POWER ACTUATED DENTAL APPLIANCE

[75] Inventor: John B. Fattaleh, Phoenix, Ariz.

[73] Assignee: Porta-Pro Incorporated, Boulder, Colo.

[21] Appl. No.: 751,251

[22] Filed: Dec. 17, 1976

[51] Int. Cl.² .............................................. A61C 3/06
[52] U.S. Cl. ................................................... 32/59
[58] Field of Search ................. 32/58, 59, 26, 27; 128/62 A; 30/45

[56] References Cited

U.S. PATENT DOCUMENTS

| | | | |
|---|---|---|---|
| 2,202,299 | 5/1940 | Pelkey | 32/59 |
| 3,242,516 | 3/1966 | Cantor | 128/62 A |
| 3,703,170 | 11/1972 | Ryckman, Jr. | 128/62 A |
| 3,802,420 | 4/1974 | Moffat et al. | 128/62 A |
| 3,826,004 | 7/1974 | Graceffo | 32/58 |
| 3,848,336 | 11/1974 | Copeland | 32/59 |
| 3,902,247 | 9/1975 | Fleer et al. | 32/22 |
| 3,921,298 | 11/1975 | Fattaleh | 32/59 |
| 3,939,599 | 2/1976 | Henry et al. | 32/59 |

Primary Examiner—Louis G. Mancene
Assistant Examiner—John J. Wilson
Attorney, Agent, or Firm—Warren F. B. Lindsley

[57] ABSTRACT

A slim-line hand-held battery-operated dental appliance having detachable head for individual use and including carrying and storing case electrified for recharging the appliance in the case.

4 Claims, 11 Drawing Figures

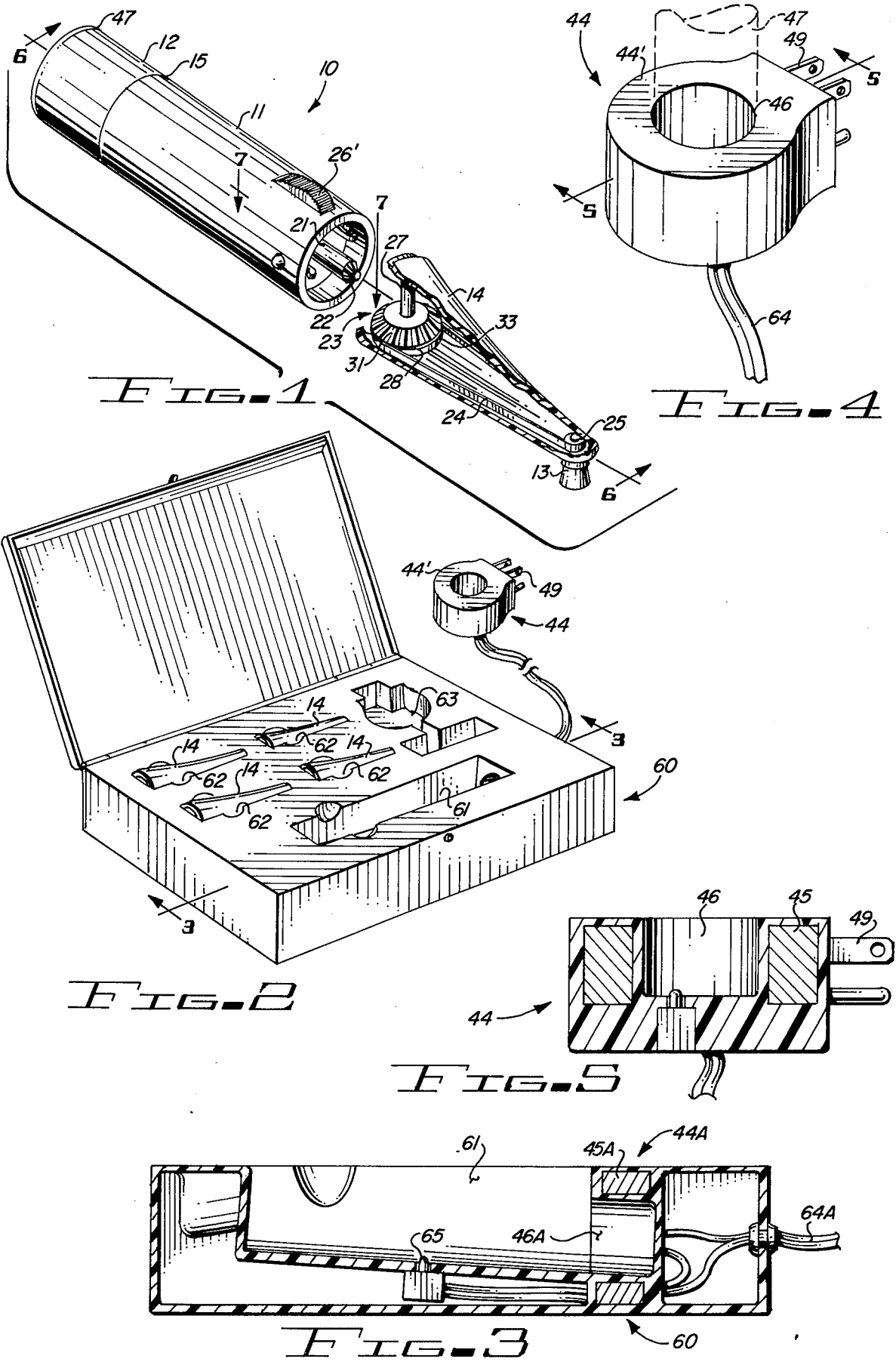

SELF CONTAINED POWER ACTUATED DENTAL APPLIANCE

BACKGROUND OF THE INVENTION

This invention is an improvement over U.S. Pat. No. 3,921,298, entitled DENTAL AND SURGICAL APPLIANCE, granted Nov. 25, 1975 to the same inventor.

Recent advances in dental technology have contributed immeasureably toward improved dental care and reduced pain and discomfort of the patient during treatment. Quieter, faster rotary cutting equipment developed in the 1950's has alleviated the discomfort associated with drilling in preparation for the filling of cavities. Modern dental hand pieces operating at speeds in excess of 500,000 revolutions per minute greatly reduce the vibration heretofore the chief causes of pain.

While the effectiveness of this modern high-speed equipment leaves little to be desired in terms of performance in the dental office, technology developments in home-care dental appliances have been lacking.

Dental practitioners recommend that a patient visit his dentist twice a year to have his or her teeth cleaned and polished. However, stains or blemishes do form on the teeth between visits which cannot be removed by the ordinary toothbrush. While these stains or blemishes may not be injurious to the teeth, they are unsightly and are a source of annoyance to persons who like to have their teeth free of stains and blemishes at all times.

Unduly high temperatures and undue abrasion of the enamel of the teeth will cause injury to the teeth. Dental practitioners take precautions, when polishing a patient's teeth, to prevent an undesirable rise in temperature and undue abrasion of the enamel of the teeth due to the friction between the teeth and polishing tool. The ordinary layman, however, is unaware of the precautions necessary to prevent injury to the teeth and it is impractical, if not dangerous, for him to undertake the polishing of his own teeth with most devices now known and used by dental practitioners.

In the dental field, as well as the general field of medicine, it is necessary to take extraordinary steps to ensure that the instruments or parts thereof used upon a patient and in his mouth are clean. Further, since a given appliance, even for home use, may be used by more than one individual, it is necessary that those portions used on the patient or in his or her mouth be detachable and/or replaceable for sanitation reasons.

Most known self-contained power-driven instruments are bulky in size and cannot easily reach cavities in the mouth. Recent advances in the development of small rechargeable batteries have permitted their application to a number of portable cordless electric appliances including toothbrushes, grass clippers and carving knives and the desirability of further extending the application of such batteries to include a battery-operated dental drill, polisher and surgical cutting tool is needed.

SUMMARY OF THE INVENTION

In accordance with the invention claimed, a cordless electric appliance such as, for example, a dental drilling polishing and cutting appliance is provided which effectively overcomes the important disadvantages associated with conventional dental tools currently used.

It is, therefore, one object of this invention to provide an improved slim-line electric appliance for rotary drilling, cutting and polishing operations.

Another object of this invention is to provide a novel electric battery-operated appliance utilizing a mechanical driving means which may be concealed within a compact, slender, tapered housing with the tool at its tapered end which permits easy access to all areas surrounding the patients' teeth and gums.

A further object of this invention is to provide a portable and inexpensive device for the polishing of teeth or other heat-sensitive surfaces which can be safely used in the home by an ordinary layman without injury to the teeth or other surfaces.

A still further object of this invention is to provide a portable dental appliance having a detachable and/or replaceable housing portion which enters or is closely adjacent the user's mouth for sanitary reasons, thereby rendering such an appliance useable by more than one member of a family.

A still further object of this invention is to provide a hand-held electric self-contained appliance which is particularly slim at its tool-supporting end for reaching into cavities hard to reach in the human body, such as the mouth.

Further objects and advantages of the invention will become apparent as the following description proceeds and the features of novelty which characterize this invention will be pointed out with particularity in the claims annexed to and forming a part of this specification.

BRIEF DESCRIPTION OF THE DRAWINGS

FIG. 1 is an exploded perspective view of a cordless electric appliance embodying the invention.

FIG. 2 is a perspective view of a portable case for carrying, storing, and recharging the disclosed dental appliance.

FIG. 3 is a cross-sectional view of FIG. 2 taken along the line 3—3.

FIG. 4 is an enlarged perspective view of an induction coil for use in recharging the batteries mounted in the disclosed dental appliance of FIG. 1.

FIG. 5 is a cross-sectional view of FIG. 4 taken along the line 5—5.

DESCRIPTION OF THE PREFERRED EMBODIMENT

Figure 6:
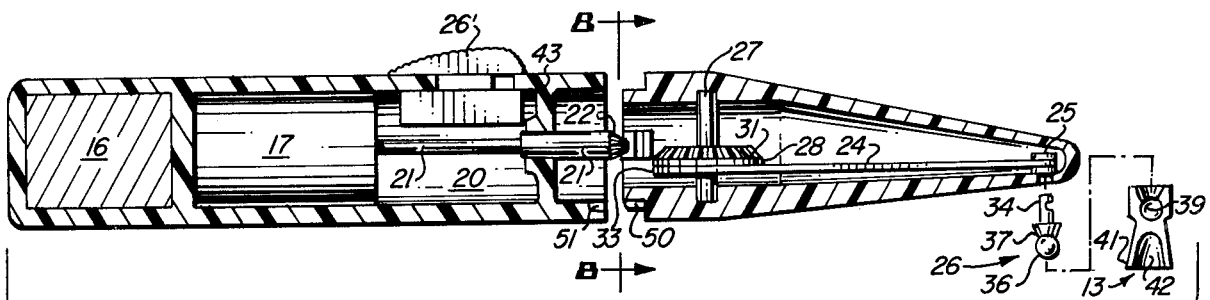
FIG. 6 is a cross-sectional view of FIG. 1 taken along the line 6—6.

Referring more particularly to the drawing by characters of reference, FIG. 1 illustrates a cordless electric dental drilling and polishing appliance 10 in a slender, slim-line elongated housing comprising a main housing 11, a detachable battery housing 12, and a rotary polishing cup 13 mounted at the tapered tip end of a long slender detachable neck section 14 of housing 11.

The battery housing is cylindrical in form and of suitable dimensions to contain a commercially available battery of appropriate rating to operate the appliance.

The main housing 11 tapers from a circular cross-sectional configuration at its end 15 which attaches to battery housing 12 to a slender configuration of neck 14. The dimensions of neck 14 of housing 11 are large enough to house the mechanical drive train incorporated within apparatus 10 for driving head 13 but small enough to readily fit into the cavities of the mouth. The slender neck area 14 is straight as shown in FIG. 1 but is modified in FIG. 10 and provided with a slight concave configuration to make it easier to handle, manipulate and fit into the mouth of the patient.

The internal parts contained within battery housing 12, as illustrated by views of FIGS. 1 and 6, include a charging cell 16 and a battery 17. The recharging cell 16, as shown in the wiring diagram of FIG. 9, contains a transformer secondary winding 18, rectifiers 19, and induction coil 45 which supply charging current to battery 17 during recharging operations if a suitable on-off switch 65 is engaged and closed by the battery end of housing 11 when it is inserted in opening 45 of charger 44, as will be explained.

The main housing 11 contains a direct current motor 20 having a shaft 21 projecting forwardly toward neck 14 and carrying at its forward end a bevel gear 22. A gear-and-pulley combination 23 is in meshing engagement with bevel gear 22 and drives a drive belt 24, pulley 25 and accessory chunk 26.

Motor 20 is normally energized from battery 17 with connection between motor 20 and battery 17 controlled by on-off switch 26. Bevel gear 22 is fixedly attached to shaft 21 and rotates at the same rate as motor 20. Gear-and-pulley combination 23 has the form of a wheel-and-hub arrangement with hub 27 projecting above the upper plane surface of wheel 28. About the periphery of the top surface of wheel 28 is a set of gear teeth 31 appropriately dimensional to mesh with the teeth of bevel gear 22. Gear-and-wheel combination 23 is rotatably anchored by means of hub 27 to the top and bottom walls of the inner surface of neck section 14 of housing 11. The plane of wheel 28 lies parallel to the beveled edge of gear 22 at the point on the underside of gear 22 which teeth 31 are engaged by the teeth of gear 22. By virtue of the special design of the gear-and-pulley combination 23 which allows this manner of orientation with respect to gear 22, these two parts are compactly arranged within section 14 of housing 11 when section 14 detachably engages housing 11.

Pulley 25, which is rotatably mounted in the tip of neck section 14, is coupled to gear-and-pulley combination 23 by means of drive belt 24. Wheel 28 has an annular groove 33 cut into the cylindrical surface of its rim to accommodate belt 24, which is also engaged by pulley 25.

Because pulley 25 has a substantially smaller diameter than wheel 28, pulley 25 turns at a proportionately higher speed than wheel 28 or gear 22. Thus, for a given speed of rotation for pulley 25 which is desirably high, the speed of rotation of gear 22 and the speed of gear-and-pulley combination 23 are relatively low with the lower speeds contributing toward reduced wear and longer life of these parts.

Accessory chuck 26 may have a non-cylindrical upper end shown more clearly in U.S. Pat. No. 3,921,298, referred to above which fits snugly inside a similarly shaped hollow axis of pulley 25 from either side of the housing and is secured therein by its shape. If the upper end of chuck 26 is cylindrical, it may be secured in the hollow axis of pulley 25 by means of a rectangular key which is driven into a keyway or slot. This slot (not shown) runs lengthwise along the portion of chuck 26 which fits inside pulley 25. The lower end of chuck 26 is a spherical knob 36 topped by a flared crown 37. Knob 36 and its flared crown 37 are shaped to conform with the inner surfaces of a complementary cavity 39 formed inside the top part of accessory 13, all described in detail in U.S. Pat. No. 3,921,298. Accessory 13 is molded from hard rubber or from a plastic material of similar mechanical properties and the dimensions of cavity 39 are appropriate to permit knob 37 of the chuck to be forced inside the complementary cavity 39. The elastic gripping action of the rubber or plastic material from which accessory 13 is formed thus fixedly attaches accessory 13 to chuck 26.

Accessory 13 is a conventional polishing attachment having as its working end a flared crown with a cavity 42 opening outwardly therefrom. Flexible ribs arranged radially inside cavity 42 act as polishing vanes and aid in keeping paste containing an abrasive powder inside cavity 42 between the radial vances and is worked out of cavity 42 as accessory 13 rotates and is pressed against the patient's teeth.

Motor shaft 21 may be rotatably supported at its forward end by a transverse rib 43 secured within housing 11.

The on-off switch 26 may be replaced if desired by a more elaborate control incorporating a variable resistance for the adjustment of motor speed.

Figure 9:
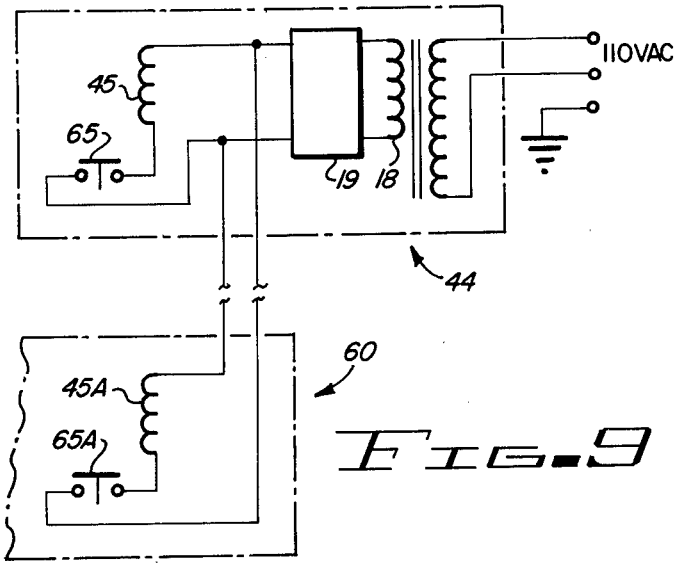
FIG. 9 is a block diagram of the recharging circuit for the battery or batteries of the appliance shown in FIG. 1.

A battery charging unit 44 comprising a housing 44' is shown in FIG. 4 and comprises a coil-shaped primary winding 45 shown in FIG. 9 mounted in housing 44' surrounding a cylindrical cup-shaped cavity 46. The open end of cavity 46 is suitably dimensioned to receive without interference the butt end 47 of appliance 10. Primary winding 45 may be connected to a conventional appliance cord (not shown) or a plug 49 of the type designed to be plugged into a utility outlet to permit energization of winding 45 from a common utility power source.

To recharge battery 17, butt end 47 of appliance 10 is inserted in cavity 46 with winding 45 energized. The secondary winding 19 contained within recharging cell 16 is located inside butt end 47 of appliance 10 and is thus positioned within cavity 46, where it is linked by magnetic flux lines set up by primary winding 45. The A-C voltage thereby induced in the secondary winding of the recharging cell 16 is rectified and delivered as a D-C charging current to battery 17.

FIGS. 6, 7, 7A and 8 disclose detail of one means for detachably connecting the neck section 14 to housing 11. As heretofore stated, it is desirable to remove the neck section from housing 11, since this is the portion of the appliance which is placed in and adjacent the mouth of a user when the appliance is used. Consequently, this neck section should be cleaned thoroughly each time it is used or an identical different neck section inserted in the appliance if a different person uses the appliance.

Figures 7, 7A:
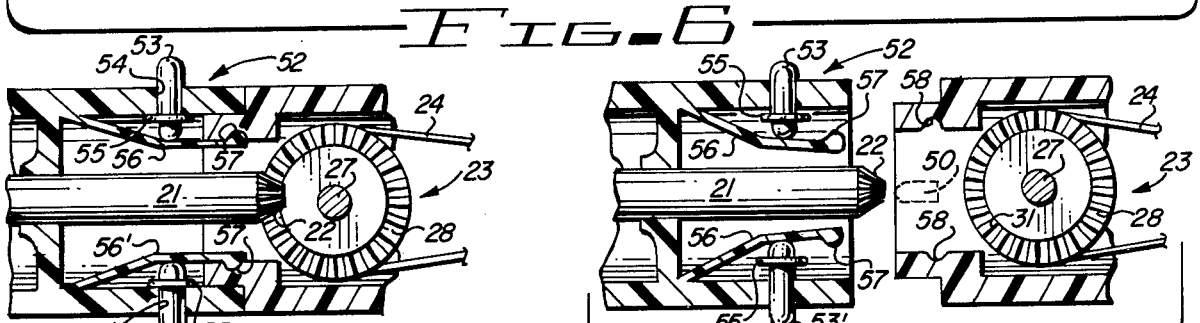
FIG. 7 is an enlarged partial view illustrating one way of detachably interconnecting the head portion to the hand-held portion of the dental appliance shown in FIG. 1.
FIG. 7A is an exploded view of the structure shown in FIG. 7 illustrating the two interlockable parts just prior to engagement.
Figure 8:
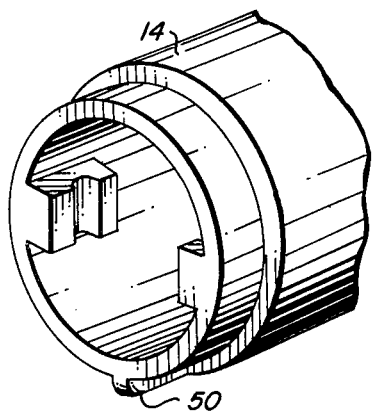
FIG. 8 is a cross-sectional view of FIG. 6 taken along the line 8—8.

As shown in FIGS. 1 and 6-8, neck section 14 may be detachably engaged with housing 11 by means of a simple slide fit, as shown, with the parts mating in a given orientation by a tongue or pin 50 and groove 51 formed in neck section 14 and housing 11, respectively. These mating parts may be firmly held in place by a pin and lever release mechanism 52. As shown in FIGS. 7 and 7A, this mechanism comprises a pair of pins 53, 53' slidably arranged in axially aligned cylindrical holes 54, 54' in housing 11. These pins each comprise a collar 55 which hold them in a given extended position when the pins are biased outwardly of housing 11 by a pair of leaf springs 56, 56'. As shown in FIGS. 7 and 7A, each of these springs are anchored at one end in housing 11 and extend outwardly of its open end and into neck section 14 when section 14 and housing 11 are in mating engagement. At the free end of each leaf spring is arranged a protrusion 57, which engages with a mating aperture 58 in the inside periphery of the hollow neck section 14 when section 14 and housing 11 are in mating end-to-end engagement.

It is obvious from the drawings that leaf springs are tensioned to simultaneously bias pins 53, 53' outward of housing 11 and their protrusions 57 into apertures 58 when the two parts are in mating engagement.

To separate the two mating parts, it is merely necessary to press pins 53, 53' inwardly, as known in the art, to push protrusions 57 of the leaf springs out of apertures 58, at which time the neck section 14 may be readily separated from housing 11.

It should be noted that when the housing 11 and neck section 14 are in mating engagement, bevel gear 22 is in driving engagement with the gear teeth 31 on wheel 28.

FIGS. 2, 3 and 5 disclose a storage or carrying case 60 having a plurality of apertures or openings for receiving in a snug fit the various parts of the dental appliance 10.

It should be noted that opening 61 is designed to receive main housing 11 together with battery housing 12 of the appliance with a plurality of openings 62 being provided to receive four neck sections 14 for the appliance. Opening 63 is contoured to receive the battery changing unit 44 and its associated electrical cord 64.

As noted from FIG. 3 of the drawing, the carrying case 60 is provided with a built-in battery changing unit 44A, comprising the secondary winding 18 and having an opening 46A for receiving therein the end of the battery housing 12 of the dental appliance. On-off switch 65A is built to extend into the opening 61 of the carrying case 60 so as to energize the charger whenever the main housing and associated battery housing are placed in opening 61 with the end of the battery housing 12 extending into opening 46A and the electric cord 64A and associated electrical plug (not shown) connected to a suitable source of electrical power, such as an AC 120 volt supply.

Figure 10:
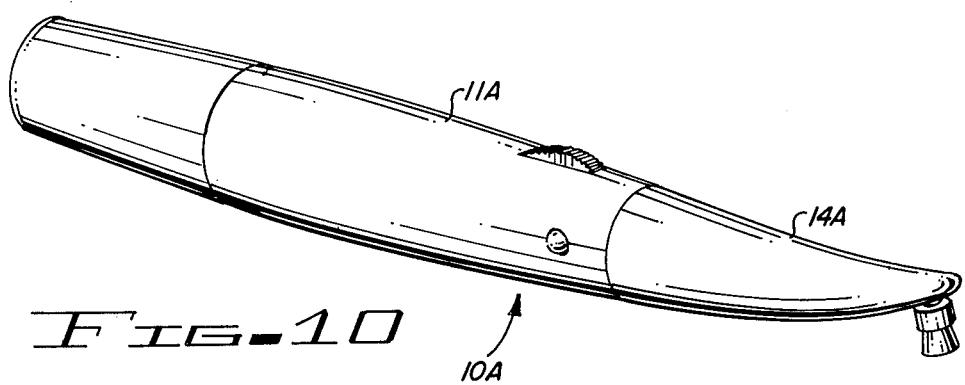
FIG. 10 is a perspective view of a modification of the outer geometrical configuration of the dental appliance shown in FIG. 1.

FIG. 10 illustrates a dental appliance 10A similar to that shown in FIG. 1 arranged in a slim-line arcuate configuration, more fully disclosed in U.S. Pat. No. 3,921,298, but differing primarily in that the replaceable neck section 14A as well as housing 11A may be of an arcuate configuration.

It should be recognized that a variety of implement attachments may be utilized with appliances 10 and 10A in place of the polishing cup 13 shown in FIGS. 1 and 10. As shown in U.S. Pat. No. 3,921,298 for purposes of illustration, cutting burrs, drills, and circular cutting blades may be attached to chuck 25. Elastic inserts inside the cavities of the burrs, drills, and blade grip knob 36 in the manner of polishing cup 13.

Thus, a portable, lightweight dental drilling appliance is provided which is unencumbered by the usual flexible shaft or belt-and-pulley power train. Through the use of rechargeable or replaceable batteries a convenient and completely safe power source is made available. A variety of accessories for polishing, cutting and drilling may be utilized with the appliance.

Although but a few embodiments of the present invention have been illustrated and described, it will be apparent to those skilled in the art that various changes and modifications may be made therein without departing from the spirit of the invention or from the scope of the appended claims.

What is claimed is:

1. A dental appliance comprising:
   an elongated hollow housing extending from a hand gripping, first end to an implement supporting end, said housing comprising a first portion adjacent its first end and a second portion detachably mounted in axial alignment therewith comprising the implement supporting end,
   power means mounted within said first portion to provide a balanced handle for said tool having an optimum weight distribution,
   said power means comprising a direct current motor and a battery for energization thereof,
   said motor having a shaft extending axially of said housing at the point of engagement of said first portion with said second portion,
   a bevel gear fixedly attached to said shaft extending outwardly of said first portion for rotating at the same rate of speed as said motor,
   a switch mounted on the outer periphery of said first portion for controlling said motor,
   a drive pulley mounted in said second portion at the implement supporting end,
   a gear reduction drive mounted within said second portion and connectable with said bevel gear of said first portion and said drive pulley in said second portion when the first and second portions are interconnected,
   said gear reduction drive comprising a wheel perpendicularly mounted to the axis of said shaft within said second portion and having a set of gear teeth around its periphery for engaging with said bevel gear,
   an implement mounting means provided adjacent said implement supporting end for engaging and being driven by said drive pulley, and
   a drive belt within said second portion for connecting said drive pulley to said gear reduction means,
   said first portion of said housing comprising a compartment for containing a battery charging means at said first end of said housing in axial alignment with a battery and said direct current motor forming said power means,
   said charging means comprising one coil of an electric power rectifying means.

2. The dental appliance set forth in claim 1 wherein:
   said housing tapers from a hand gripping cylindrically sloped first end to the implement supporting end.

3. The dental appliance set forth in claim 1 wherein:
   at least said second portion of said housing is provided with an arcuate configuration.

4. The dental appliance set forth in claim 1 in further combination with:

a storage and carrying case for said appliance comprising bottom member having a plurality of apertures conformed to relatively snugly fit the detachable parts of said appliance, one of said apertures of said bottom conformed to receive said first portion of said housing with said one end of said housing fitting into a collar forming a further part of said charging means, said further part comprising a second coil of the electric power rectifying means, said collar being formed in the bottom of said case around said one end of said housing when said first portion is placed in said one of said apertures, and an on-off switch mounted in said case and extending into said one of said apertures for electrically connecting said second coil to a source of alternating current when said first portion of said housing is snugly fitted into said one of said apertures.

* * * * *